United States Patent [19]

Crandall

[11] Patent Number: 5,560,910
[45] Date of Patent: Oct. 1, 1996

[54] TOPICAL ANTI-INFLAMMATORY COMPOSITION AND METHOD

[76] Inventor: Wilson T. Crandall, Rte. 616, Jolly Hill, Ft. Defiance, Va. 24437

[21] Appl. No.: 296,710

[22] Filed: Aug. 26, 1994

[51] Int. Cl.$^6$ .......................... A61K 38/46; A61K 38/48; A61K 31/16; A01N 33/06
[52] U.S. Cl. .................... 424/94.63; 424/94.64; 424/94.65; 424/94.67; 514/611; 514/613; 514/627
[58] Field of Search .............................. 424/94.63, 94.64, 424/94.65, 94.67; 514/627, 611, 613

[56] References Cited

U.S. PATENT DOCUMENTS

| | | | |
|---|---|---|---|
| 3,905,869 | 9/1975 | Hidaka et al. | 514/23 |
| 3,932,618 | 1/1976 | Fujii et al. | 424/94.1 |
| 4,507,286 | 3/1985 | Vellini | 514/23 |
| 5,178,879 | 1/1993 | Adekunle et al. | 124/484 |
| 5,254,338 | 10/1993 | Sakai et al. | 424/443 |

OTHER PUBLICATIONS

Taussig, S. J., "The mechanism of the physiological action of Bromelain", *Medical Hypotheses*, 6: 99–104, 1980.

Hoo–Kyun, C., et al. "Transdermal delivery of bioactive peptides: The Effect of n–Decylmethyl Sulfoxide, pH, and Inhibitors on Enkephalin Metabolism and Transport", *Pharm. Res.*, vol. 7, No. 11, pp. 1099–1106, 1990.

Hoo–Kyun, C., et al. "Some General Influences of n–Decylmethyl Sulfoxide on the Permeation of Drugs Across Hairless Mouse Skin", *Soc. Invest. Derm.*, vol. 96 pp. 822–826, 1991.

Willimann, H., et al., "Lecithin Organogel as Matrix for Transdermal Transport of Drugs", *J. Pharm. Sci.*, vol. 81, 1992.

Scartazzini, et al., *J. Phys. Chem.*, vol. 92, pp. 829–833, 1988.

Luisi, P. L. et al., *Colloid Polym Sci.*, vol. 268, pp. 356–374, 1990.

Colpaert et al. *Life Science* B2(16). pp. 1827–1834. 1983.

Lam et al. *Neurosci Letters* 105(1–2) pp. 155–158. 1989.

*Primary Examiner*—Michael G. Wityshyn
*Assistant Examiner*—L. Blaine Lankford
*Attorney, Agent, or Firm*—Jones & Askew

[57] ABSTRACT

The present invention comprises compositions and methods that are useful for topically treating inflammation caused by a wide variety of diseases. The compositions comprise an effective amount of a proteolytic enzyme, such as bromelain, in combination with capsaicin in a pharmaceutically acceptable carrier.

4 Claims, No Drawings

TOPICAL ANTI-INFLAMMATORY COMPOSITION AND METHOD

TECHNICAL FIELD

The present invention is related to a topical anti-inflammatory composition and method. More particularly, the present invention is related to the transdermal delivery of macromolecules, such a bromelain, for relief of pain or pruritus due to inflammation.

BACKGROUND OF THE INVENTION

Many patients with localized pain due to arthritis, bursitis, sprain or muscle strain, bruises or hematomas cannot tolerate conventional nonsteroidal anti-inflammatory drugs, commonly known as NSAIDS. In addition, topical administration of conventional NSAIDS has largely been ineffective because only a therapeutically ineffective amount of the drug can penetrate the skin. In addition, indications such as acne, psoriasis and eczema are typically refractory to topical or oral administration of NSAIDS.

Bromelain is a protease composition that is isolated from pineapple. The composition has been reported to have anti-inflammatory activity when administered orally or parenterally (see Taussig, S. J., "The mechanism of the physiological action of Bromelain", *Medical Hypotheses*, 6; 99–104, 1980). Commercially available bromelain used in the manufacture of pharmaceuticals is not a chemically homogeneous substance, but the principal component is a proteolytic enzyme that is a glycoprotein. The molecular weight of the protease in bromelain is approximately 33,000 Daltons.

Capsaicin is an oleoresin obtained by extracting cayenne pepper with ether. The synthetic capsaicin is trans-8-methyl-vanillyl-6-nonenamide. Capsaicin gels have been described in U.S. Pat. No. 5,178,879 as being effective in treating topical pain. In addition, capsaicin is available commercially in over-the-counter compositions intended for pain relief including lotions such as HEET, OMEGA OIL, SLOAN'S LINIMENT and ZOSTRIX.

Bromelain has been reported to be an anti-inflammatory agent, an inhibitor of platelet aggregation, an agent that increases proteolytic and fibrinolytic activity in blood, and as a selective prostaglandin inhibitor. Bromelain has been administered by injection and has been reported to be effective after oral administration. However, because bromelain is a macromolecule, it cannot be administered transdermally using prior art formulations.

What is needed is an anti-inflammatory composition that is effective in treating a wide variety of inflammatory conditions by topical application of the composition. The anti-inflammatory composition should not have the side effects associated with prior art non-steroidal anti-inflammatory agents.

SUMMARY OF THE INVENTION

The present invention addresses the needs in the prior art by providing an anti-inflammatory composition containing a proteolytic enzyme, preferably bromelain, and capsaicin. The anti-inflammatory composition is capable of being administered transdermally to a human or animal. The present invention is a topical anti-inflammatory composition comprising an effective amount of bromelain, an effective amount of capsaicin, and a pharmaceutically effective penetrating agent. Preferred penetrating agents are effective amounts of n-decylmethyl sulfoxide and lecithin organogel.

The present invention provides an easy and safe method of administering an effective anti-inflammatory macromolecule that, in the prior art, could only be administered parenterally or orally. By administering the composition topically directly at the site of the inflammation, the present invention provides a more effective means of treating the inflammation. The present invention is useful for treating a variety of inflammatory indications including neuralgias, rheumatoid arthritis, sprains, bursitis, myositis, carpal tunnel syndrome, chondromalacia, eczema, inflammation due to infections by microorganisms, psoriasis and integumental pain.

In addition, the present invention provides a alternative composition and method to conventional NSAIDS for treating inflammation. The present composition does not have the side effects that are often seen with NSAIDS. Some of these side effects include, but are not limited to, somnolence, confusion, gastric upset, GI bleeding, chondrocyte dysfunction and kidney damage.

In one embodiment, the composition of the present invention comprises bromelain and capsaicin in a pharmaceutically acceptable composition containing n-Decylmethyl sulfoxide. The present invention can include other pharmaceutically acceptable components such as gelling agents, compounding agents, scents and the like. In an especially preferred formulation, the composition further contains a lecithin organogel. The combination of a transdermal formulation of bromelain and capsaicin act synergistically to reduce pain. The composition of the present invention can also include other pharmaceutically active agents such as antibacterial, antifungal, antiprotozoal or antiviral agents.

The present invention also includes methods for topically treating inflammation due to a wide variety of causes comprising the step of topically administering a therapeutically effective amount of a composition comprising bromelain and capsaicin in a pharmaceutically acceptable vehicle, the vehicle including n-decylmethyl sulfoxide and/or lecithin organogel.

Accordingly, it is an object of the present invention to provide a composition and method for topically treating inflammation.

It another object of the present invention to provide a composition and method for topically treating arthritis.

It is yet another object of the present invention to provide a composition and method for topically treating bursitis.

It is yet another object of the present invention to provide a composition and method for treating acne, psoriasis and eczema.

It is yet another object of the present invention to provide a composition and method for treating flea allergy, dermatitis, and atopy.

It is yet another object of the present invention to provide a composition and method for topically treating inflammation that is safe and effective and does not have the side effects of conventional NSAIDS.

These and other objects, features and advantages of the present invention will become apparent after a review of the following detailed description of the disclosed embodiments and the appended claims.

DETAILED DESCRIPTION

The present invention is a composition and method for topically treating inflammation caused by a wide variety of causes including, but not limited to, arthritis, bursitis, sprains, muscle strains, bruises, and hematomas. The present invention is a composition containing bromelain and capsaicin. The composition further comprises n-decylmethyl sulfoxide and/or lecithin organogel as agents to increase the transport of bromelain across the skin.

Generally, the composition of the present invention comprises bromelain (PCAA, Kinghurst, Houston, Tex.) at a concentration of between approximately 0.5% and 40% by weight, with a preferred concentration of between approximately 10% and 25% by weight, with the most preferred concentration of approximately 15% by weight. It should be understood that other proteolytic enzymes can be used in the present invention, including but not limited to, collagenase, gelatinase, and elastase.

The anti-inflammatory composition of the present invention also contains capsaicin. The capsaicin can be either naturally occurring capsaicin oleo resin (PCAA, Kinghurst, Houston, Tex.) which is commonly extracted from cayenne pepper with an organic solvent such as ether or can be synthetic capsaicin, trans-8-methyl-vanillyl-6-nonenamide (PCAA 10925 Kinghurst, Houston, Tex.). The capsaicin is present in the transdermal anti-inflammatory of the present invention at a concentration of between approximately 0.01% and 0.1% by weight, with a preferred concentration of between approximately 0.015% and 0.09% by weight, with the most preferred concentration of approximately 0.025% by weight.

The present invention also includes a pharmaceutically acceptable penetrating agent. A preferred penetrating agent is n-decylmethyl sulfoxide. n-Decylmethyl sulfoxide has been described as an agent that is useful in facilitating the delivery of small molecules transdermally (see Hoo-Kyun, C., et al. "Transdermal delivery of bioactive peptides: The Effect of n-Decylmethyl Sulfoxide, pH, and Inhibitors on Enkephalin Metabolism and Transport", *Pharm. Res.*, Vol. 7, No. 11, pgs. 1099–1106, 1990 and Hoo-Kyun, C., et al. "Some General Influences of n-Decylmethyl Sulfoxide on the Permeation of Drugs Across Hairless Mouse Skin", *Soc. Invest. Derm.*, Vol. 96, pgs. 822–826, 1991, both of which are incorporated herein by reference). However, there is nothing in the literature known to the inventors that would indicate that n-decylmethyl sulfoxide would be effective in facilitating the transport of macromolecules, such as bromelain, across the skin.

n-Decylmethyl sulfoxide (PCAA 10925 Kinghurst, Houston, Tex.) is present in the transdermal anti-inflammatory of the present invention at a concentration of between approximately 0.1% and 1% by weight, with a preferred concentration of between approximately 0.2% and 0.8% by weight, with the most preferred concentration of approximately 0.5% by weight.

Another preferred penetrating agent is lecithin organogel. Lecithin organogels have been described as vehicles that are useful in facilitating the delivery of low molecular weight compounds transdermally (Willimann, H., et al., "Lecithin Organogel as Matrix for Transdermal Transport of Drugs", *J. Pharm. Sci.*, Vol. 81, 1992, which is incorporated herein by reference). The lecithin organogels are obtained by adding small amounts of water to a solution of lecithin in organic solvents. Generally, lecithin organogels are prepared at room temperature by first dissolving lecithin in an organic solvent such as isopropyl palmitate or cyclooctane and then adding enough water while stirring to obtain the desired gel. Preparation of a variety of lecithin gels, all of which are appropriate in practicing the present invention, are described in Scartazzini, et al. *J. Phys. Chem*, Vol. 92, pgs. 829–833 and Luisi, P. L. et al. Colloid Polym Sci. Vol. 268, pgs. 356–374, 1990, both of which are incorporated herein by reference. The lecithin organogel preferably comprises 1 to 1 (weight/vol) of soy lecithin (PCAA, Kinghurst, Houston, Tex.) to isopropyl palmitate (PCAA, Kinghurst, Houston, Tex.) (1 g:1 ml). Water is added to form the desired gel. Other penetrating agents may be used in the composition of the present invention.

A gelling agent optionally may be added to the formulation. Gelling agents that are suitable for use in the present invention include, but are not limited to, lecithin organogel, cellulose ethers, alginates, polyacrylates, bentonite, gelatin, tragcanth, polyvinylpyrrolidone, polyvinyl alcohol, and polyoxyethylene/polyoxypropylene block copolymers.

Optionally, a preservative, such as sorbic acid, can be added to the composition. Other preservatives well known to those of ordinary skill in the art can be used in the anti-inflammatory composition.

Agents for improving the aroma of the formulation can optionally be added to the composition. A desired aroma improving agent is honey almond oil (PCAA, Kinghurst, Houston, Tex.). Other aroma improving agents include, but are not limited to, avocado oil, sesame oil, castor oil, olive oil, grapeseed oil, clove oil, groundnut oil, corn oil, hazelnut oil, jojoba oil, carthamus oil and wheatgerm oil, The oils can be added individually or in combination. Stabilizers, antioxidants, preservatives, humectants, regreasing agents, solvents or auxiliaries can be added to improve stability and/or adhesiveness of the formulations.

In addition, antimicrobial agents can be optionally added to the anti-inflammatory composition of the present invention if required. Addition of an antimicrobial agent is desirable when treating inflammatory conditions associated with acne, psoriasis or eczema.

The method of the present invention includes topical administration of a pharmaceutically acceptable composition containing bromelain and capsaicin with either n-decylmethyl sulfoxide and or lecithin organogel for treatment of inflammation. The anti-inflammatory composition of the present invention can be administered topically either once daily or several times per day depending upon the nature and severity of the inflammation being treated.

Preferably, the anti-inflammatory composition of the present invention is applied topically at the site of the inflammation. For example, for osteoarthritis of the knee, the anti-inflammatory composition of the present invention is applied topically around the knee by rubbing the composition on the skin. Typically, the anti-inflammatory composition of the present invention is applied in widths of approximately 1.5 cm, 2.5 cm or 3.5 cm. If the composition is applied to a painful joint, it can be applied directly on one side of the joint or can be evenly rubbed around the entire joint. If severe pain exists, it is helpful to apply an equal amount of the anti-inflammatory composition of the present invention on the anterior and posterior surface between 1 and 4 times daily for 2 weeks. The anti-inflammatory composition of the present invention should be applied until the pain subsides. The amount of the composition that is applied to the skin is not critical to the invention. It is important that the composition be thoroughly rubbed into the skin.

Although not wanting to be bound by the following hypothesis, it is believed that the anti-inflammatory composition of the present invention causes at least a portion of the macromolecule, for example bromelain, to be transdermally delivered to the site of the inflammation. By delivering the bromelain to the site of the inflammation, the enzyme can exert its anti-inflammatory effect. In addition, the present invention causes more capsaicin to be delivered to the inflammatory site thereby relieving pain presumably by inhibiting release of substance P.

It will be appreciated that other embodiments and uses will be apparent to those skilled in the art and that the invention is not limited to these specific illustrative examples.

EXAMPLE I

A bromelain topical composition (Bromelain 20%/PLO) is prepared as follows:

| | |
|---|---|
| Bromelain Powder | 20 g |
| Capsaicin | 25 mg |
| Honey Almond Oil | 2 ml |
| Lecithin organogel | 20 ml |
| Pluronic Gel 20% | 80 ml |

The lecithin organogel is prepared by dissolving 10 g of soy lecithin granules (PCAA, Houston Tex.) in 10 ml of isopropyl palmitate. 40 mg of sorbic acid is added as a preservative. The mixture is stirred periodically for 24 hours until the soy lecithin is dissolved. The Pluronic gel 20% is prepared by dissolving 16 g PLURONIC® 127 (BASF, Parsippany, N.J.) in 80 ml of distilled water. Add 160 mg of potassium sorbate.

The Bromelain 20%/PLO is prepared by mixing the bromelain powder with the lecithin organogel and honey almond oil until a smooth mixture is prepared. Add the Pluronic gel and mix until a gel forms. Store at room temperature.

EXAMPLE II

A bromelain roll-on formulation is prepared as follows:

| | |
|---|---|
| Bromelain | 20 g |
| Capsaicin | 25 mg |
| η-decylmethyl sulfoxide | 500 mg |
| Distilled water | 100 ml |
| Honey almond oil | 2 ml |

Stir bromelain powder into water. Add the n-decylmethyl sulfoxide and stir continuously for 2 hours. Add the honey almond oil.

EXAMPLE III

A male Pekinese had a proximal radial dislocation. The composition described in Example I was applied around the dislocated joint twice a day for 7 days. The animals gait improved 50% almost immediately.

EXAMPLE IV

A Walker coonhound had a massive lick granuloma on the left forearm. An Elizabethan collar was fitted on the dog and the composition described in Example I was applied topically on the wound. The composition was applied every 12 hours for 7 days. At the end of seven days, the wound had improved significantly.

EXAMPLE V

A female cat was diagnosed with a soft tissue infection with ferunculosis and fistulae. The inflammation was so severe, multiple skin incisions were done to prevent muscular necrosis. The composition described in Example I was mixed with a fluoroquinone antibiotic and applied topically over the infection. The composition was applied topically every 8 hours for 4 days and then every 12 hours for seven days. The cat recovered completely.

EXAMPLE VI

A walking horse was lame bilaterally in forelimbs, and hyperemic and inflamed. The composition described in Example I was applied topically and was gently rubbed completely around the leg every 12 hours. After 24 hours, the inflammation was resolving. Treatment was continued for 2 days.

EXAMPLE VII

An obese sheltie dog suffering from generalized osteoarthritis had surgery to repair an anterior cruciate ligament. The dog couldn't stand after surgery. The sutures were removed seven days after surgery. The composition described in Example II was applied topically along the suture lines every 8 hours. The dog began walking within 24 hours after application of the composition described in Example II.

It should be understood that the foregoing relates only to a preferred embodiment of the present invention and that numerous modifications or alterations may be made therein without departing from the spirit and the scope of the invention as set forth in the appended claims.

I claim:

1. A topical anti-inflammatory composition comprising an anti-inflammatory effective amount of bromelain, an anti-inflammatory effective amount of capsaicin, and a pharmaceutically effective penetrating agent wherein the penetrating agent is selected from the group consisting of n-decylmethyl sulfoxide and lecithin organogel.

2. A method of treating an inflammatory condition in a patient comprising the step of topically administering to the patient with the inflammation an anti-inflammatory composition comprising an anti-inflammatory effective amount of bromelain, an anti-inflammatory effective amount of capsaicin, and a pharmaceutically effective penetrating agent wherein the penetrating agent is selected from the group consisting of n-decylmethyl sulfoxide and lecithin organogel.

3. The method of claim 2, wherein the inflammatory condition is selected from the group consisting of neuralgia, rheumatoid arthritis, sprain, bursitis, myositis, carpal tunnel syndrome, chondromalacia, eczema, inflammation due to infections by microorganisms, psoriasis and integumental pain.

4. The method of claim 2, wherein the anti-inflammatory composition is applied topically at the site of the inflammatory condition.

* * * * *